United States Patent [19]

Shaffar

[11] Patent Number: 4,495,293

[45] Date of Patent: Jan. 22, 1985

[54] FLUOROMETRIC ASSAY

[75] Inventor: Mark R. Shaffar, Vernon Hills, Ill.

[73] Assignee: Abbott Laboratories, North Chicago, Ill.

[21] Appl. No.: 469,323

[22] Filed: Feb. 24, 1983

[51] Int. Cl.$^3$ .................. G01N 21/17; G01N 21/25
[52] U.S. Cl. ........................... 436/172; 250/461.1; 436/501; 436/537; 436/800
[58] Field of Search .......... 250/373, 458.1, 459.1, 250/461.1; 435/808; 436/86, 87, 88, 71, 95, 97, 108, 132, 164, 172, 537

[56] References Cited

U.S. PATENT DOCUMENTS

| | | | |
|---|---|---|---|
| 3,874,853 | 4/1975 | Byrnes | 436/164 X |
| 4,095,948 | 6/1978 | Hunziker | 435/808 X |
| 4,161,515 | 7/1979 | Ullman | 436/537 |
| 4,261,968 | 4/1981 | Ullman et al. | 436/537 X |
| 4,273,556 | 6/1981 | Gindler | 436/108 |

OTHER PUBLICATIONS

Willard et al., Instrumental Methods of Analysis, 4th Edition, (1968), pp. 370–395.
Tietz, *Fundamentals of Clinical Chemistry*, W. B. Saunders, (1970), pp. 87–98.
Tietz, *supra*, pp. 107–108; pp. 139–142.

Primary Examiner—Barry S. Richman
Assistant Examiner—Robert J. Hill, Jr.
Attorney, Agent, or Firm—James L. Wilcox

[57] ABSTRACT

A method is provided to fluorometrically determine a ligand in an assay solution containing the ligand, reagent system and a fluorescer wherein the intensity of the fluorescer emitted by the assay solution is related to the change in the transmittive properties of the assay solution produced by the interaction of the ligand to be determined and a reagent system capable of producing a change in the transmittive properties of the assay solution in the presence of the ligand. In addition, novel reagent compositions are provided which may be utilized to either spectrophotometrically or fluorometrically determine the concentration of a ligand in an assay solution.

12 Claims, No Drawings

FLUOROMETRIC ASSAY

BACKGROUND OF THE INVENTION

Conventional nonisotopic methods of analysis in the field of clinical medical diagnostics involve the spectrophotometric or fluorometric determination of clinically significant substances, hereinafter referred to as ligands. Such methods are highly sensitive and specific and rely upon the measurement of the change in the optical properties, that is, the transmittive or fluorescent properties of an assay solution resulting from the presence of a particular ligand in the assay solution.

In a spectrophotometric assay, the interaction in an assay solution between the ligand to be determined and a reagent system specific for the ligand, produces a detectable change in the transmittive properties of the assay solution. The change in the transmittive properties refers to the amount of light absorbed or scattered by an assay solution within a particular wavelength band when a beam of light of known intensity is passed through the assay solution. The change in the transmittive properties of an assay solution is measured by passing nonochromatic light having a known intensity through the assay solution and determining the ratio of the intensity of the transmitted or scattered light to the intensity of the incident light. The fact that nearly all ligands either absorb energy of a specific wavelength or interact in an assay solution with a particular reagent system to produce a detectable change in the transmittive properties of the assay solution, has resulted in the development of numerous specific spectrophotometric assays. Spectrophotometric assays which rely upon the measurement of the change in the transmittive properties of an assay solution as a measure of a ligand in the assay solution include, for example, assays wherein there is a change in the color of the assay solution, that is, colorimetric assays and assays wherein there is a change in the turbidity of the assay solution, that is, turbidimetric or nephelometric assays. In a colorimetric assay, the change in the transmittive properties of an assay solution is generally referred to as the absorbance of the assay solution and is dependent upon the change in the color of the assay solution due to the interaction of the ligand to be determined and reagent system specific for the ligand. The absorbance of the assay solution is related to the concentration of the ligand in the assay solution. A colorimetric assay utilizes a chromogenic reagent system capable of interacting in an assay solution with the particular ligand of interest, to produce a detectable change in the transmittive properties, specifically the color, of the assay solution. Numerous chromogenic reagent systems useful in the determination of specific ligands have been developed and are commercially available. The principle of turbidimetric assays is to determine the amount of light scattered or blocked by particulate matter as light passes through an assay solution. In a turbidimetric assay, the ligand of interest interacts with a reagent system specific for the ligand to form a suspension of particles in the assay solution. As a beam of light having a known intensity is passed through an assay solution, the suspension of particles formed by the interaction of the ligand and reagent system, blocks or scatters the incident light thereby reducing the intensity of the light transmitted through the assay solution. The change of the transmittive properties in a turbidimetric assay refers to the decrease in the intensity of the light transmitted through an assay solution and is related to the amount of incident light that is scattered or blocked by the suspension of particles and depends upon the number of particles present and the cross-sectional area of such particles. A nephelometric assay is similar to a turbidimetric assay in that the ligand of interest interacts with a reagent system specific for the ligand to form a suspension of particles in the assay solution. In a nephelometric assay, the change in the transmittive properties of the assay solution is also related to the amount of incident light scattered or blocked by the suspension of particles but unlike a turbidimetric assay wherein the intensity of the light transmitted through the assay solution is measured, the scattered or blocked light is measured at an angle to the light incident to the assay solution. Therefore, in a nephelometric assay the change in the transmittive properties refers to the difference in intensities of light incident to the assay solution and light scattered at an angle to the incident light. Turbidimetric and nephelometric assays are utilized in the analysis of blood, urine, spinal fluid, etc., for the determination of ligands such as proteins wherein there is no comparable colorimetric assay due to the lack of an effective chromogenic reagent system. Yoe and Klimman in *Photoelectric Chemical Analysis*, Vol. II: *Nephelometry*, Wiley & Sons, Inc., New York, 1929, describe various nephelometric assays.

Typically in the fluorometric assay, a ligand in an assay solution is chemically or immunologically transformed into a fluorescent complex or conjugate thereby producing a detectable change in the fluorescent properties of the assay solution. The change in the fluorescent properties of the assay solution is measured by exciting the fluorescent complex or conjugate produced, with monochromatic light of a wavelength within the excitation wavelength band of the fluorescer and measuring the intensity of the emitted light at a wavelength within the emission wavelength band of the fluorescer. The fluorescent intensity of the emitted light is related to the concentration of the ligand. However, the intensity of the fluorescence emitted by the assay solution may be inhibited when the ligand to be determined complexes with nonfluorescent interferences such as proteins or phosphates present in the sample, or when the sample containing the ligand to be determined has sufficient color so to act as a filter and thereby reduce the intensity of the emitted fluorescence. It is well recognized that in order to maximize the sensitivity and specificity of a fluorometric assay, these inhibiting factors if present, must be overcome, either by removal of the nonfluorescent interferences or color producing material prior to the analysis, or by compensating for the presence of such factors using an internal standard added to a second aliquot of sample and carrying out the entire assay procedure using the aliquot containing the internal standard.

It is an object of the present invention to provide a method to fluorometrically determine a ligand in an assay solution wherein the intensity of the fluorescence emitted by the assay solution is related to the change in the transmittive properties produced by the interaction of the ligand to be determined and a reagent system capable of producing a change in the transmittive properties of the assay solution in the presence of the ligand. In addition, it is an object of the present invention to provide a novel reagent composition which may be utilized to either spectrophotometrically or fluorometrically measure the concentration of a ligand in an assay solution.

SUMMARY OF THE INVENTION

The present invention encompasses a method for determining a ligand in a sample suspected of containing said ligand, wherein said method comprises combining to form an assay solution: said sample, an effective amount of a fluorescer; and an effective amount of a reagent system which in the presence of the ligand to be determined is capable of providing a change in the transmittive properties of the assay solution within a wavelength band that overlaps the excitation and/or emission wavelength band of the fluorescer; irradiating the assay solution with light having a wavelength within the excitation wavelength band of the fluorescer; and then measuring the intensity of the fluorescence emitted by the assay solution as a measure of the concentration of the ligand in the sample.

The present invention further relates to novel reagent compositions for fluorometrically determining a ligand in a sample suspected of containing said ligand, wherein the reagent compositions comprise an effective amount of a reagent system capable of providing a change in the transmittive properties of a solution containing the ligand and an effective amount of a fluorescer having an excitation and/or emission wavelength band that overlaps the wavelength band associated with the change in the transmittive properties of a solution containing the reagent and ligand.

DETAILED DESCRIPTION OF THE INVENTION

In accordance with the method of the present invention, a ligand in a biological sample is determined by combining in an assay solution said sample, an effective amount of a reagent system, and an effective amount of a fluorescer. The assay solution is irradiated with light having a wavelength within the excitation wavelength band of the fluorescer and the intensity of the fluorescer emitted by the assay solution is measured as an indication of the concentration of the ligand in the sample. The intensity of the fluorescence emitted by the assay solution is proportional to the change in the transmittive properties of the assay solution resulting from the interaction of the ligand and reagent system.

As used herein, the term "change in the transmittive properties of the assay solution" refers to the amount of light absorbed or scattered by an assay solution within a particular wavelength band when a beam of light of known intensity is passed through the assay solution and generally depends upon the change in the color or turbidity of the assay solution. In particular, the change in the transmittive properties refers to the change in the amount of light absorbed or scattered by the assay solution within a particular wavelength band wherein the change results substantially from the interaction of the ligand and a reagent system specific for the ligand. The change in the transmittive properties is generally measured by passing monochromatic light having a known intensity through the assay solution and determining the ratio of the intensity of the transmitted or scattered light to the intensity of the incident light. The change in the transmittive properties, that is, the change in the amount of light absorbed or scattered by the assay solution within a particular wavelength band is proportional to the concentration of the ligand in the assay solution. It has now been found that in an assay solution containing a ligand, reagent system and fluorescer, the change in the transmittive properties, within a wavelength band that overlaps the excitation and/or emission wavelength band of the fluorescer, resulting from the interaction of the ligand and reagent system also results in a proportional change in the intensity of the fluorescence emitted by the assay solution. Therefore, in accordance with the method of the present invention, the change in the intensity of the fluorescence emitted by the assay solution is proportional to the concentration of the ligand in the assay solution. It should be noted that in accordance with the method of the present invention, the change in the intensity of the fluorescence emitted by an assay solution containing the ligand to be determined, reagent system and fluorescer, when compared to the intensity of the fluorescence emitted by an assay solution containing only the reagent system and fluorescer, is due entirely to the change in the transmittive properties produced by the interaction of the ligand and reagent system. There is no reaction, either chemical or immunological between the fluorescer and any other component, namely, the ligand to be determined or reagent system, in the assay solution. Therefore, the intensity of the fluorescence emitted by the assay solution does not depend upon the intermolecular distance between the fluorescer and any chromogenic substances or suspended particles that may be present in the assay solution.

The ligands determinable by the method of the present invention include clinically significant substances which are capable of being colorimetrically, turbidimetrically or nephelometrically determined. That is, the ligand must be capable of interacting with a reagent system to produce a detectable change in the transmittive properties related to the concentration of the ligand in the assay solution. Representative of ligands that may be assayed in accordance with the method of the present invention include, for example, glucose, uric acid, cholesterol, creatinine, lactate, lactate dehydrogenase (LDH), triglycerides, immunoglobulins, cholinesterase, serum glutamate oxalactate transaminase (SGOT), serum glutamate pyruvate transaminase (SGPT), creatine phosphokinase (CPK), ethanol, total protein, albumin, calcium, bilirubin, blood urea nitrogen (BUN), ammonia, magnesium, phosphorous, chloride and the like.

The term "fluorescer" refers to a compound or composition having fluorescent characteristics related to the transmittive characteristics of a solution containing a reagent system and ligand. In particular, the excitation or emission wavelength band associated with the fluorescer, must overlap the wavelength band associated with the change in the transmittive properties of the assay solution resulting from the interaction of the ligand and the reagent system. In addition, as mentioned there is no chemical or immunological binding between the fluorescer and the ligand to be determined or the reagent system. Another consideration concerns the pH of the reagent system. The fluorescer must fluoresce within the pH range effective for the reagent system to interact with the ligand to be determined. In addition, the fluorescers effective in the methods of the present invention are fluorescent in the unbound and uncomplexed state. In a colorimetric assay, the excitation wavelength band or the emission wavelength band associated with the fluorescer, must at least partially overlap the absorption wavelength band associated with the interaction of the ligand and chromogenic reagent system. For maximum assay sensitivity, it is preferred that absorption wavelength band resulting from the interaction of the ligand and chromogenic reagent system, overlap both the excitation wavelength band and the emission band associated with the fluorescer. In a turbidimetric or nephelometric assay, the excitation or the emission wavelength band associated with the fluorescer must at least partially overlap the wavelength band wherein the turbidity of an assay solution containing the ligand and turbidimetric or nephelometric reagent system is measured. As used herein, the "overlap" of the wavelength band associated with the change in the transmittive properties and the excitation and/or emission wavelength band of the fluorescer, refers to either a partial or total overlap of the respective wavelength bands.

A wide variety of fluorescers may be employed in the method of the present invention. As already indicated, the choice of the fluorescer will depend upon the particular ligand to be determined and reagent system employed. Representative of the classes of fluorescers that may be employed in the methods of the present invention include for example fluoresceins, rhodamines, flavins, coumarins, napththalenes, acridines, anthracenes, polynuclear fused hydrocarbons, stilbenes, anthranilic acids, aminostyrylpyridines, quinolines, salicylic acids, cyanines, oxonols, phenanthidines, fluorescamines, as well as derivatives and salts thereof. Illustrative of specific fluorescers that may be employed include, for example, eosin, rhodamine, aminonaphthalene sulfonate, acriflavin, fluorescein, dihydroxybenzoic acid, hydroxyquinoline, NADH, riboflavin, brilliant sulfaflavin, quinine, naphtholsulfonic acid, thioflavin, coumarin, acridine orange, 8-anilino-1-naphthalene sulfonic acid, oxazine, umbelliferone, acridine, resorufin, and derivatives and salts thereof. The selection of a fluorescer effective in the methods of the present invention is readily ascertained by one of ordinary skill in the art. The term "effective amount of a fluorescer" as used herein, refers to a concentration of fluorescer in an assay solution sufficient to produce a detectable change in the intensity of the fluorescence emitted by the assay solution when a ligand and reagent system specific for the ligand is added to the assay solution. Such effective amounts are generally ascertained by one of ordinary skill in the art and depend upon one or more factors such as for example, the specific reagent system, ligand to be determined, the specific fluorescer or instrumentation utilized to measure the intensity of the fluorescence.

The term "reagent system" as used herein refers to a chemical system containing one or more reagents which in the presence of the ligand of interest produces a change in the transmittive properties of an assay solution within a wavelength band that overlaps the excitation and/or emission wavelength bands of a fluorescer. Reagent systems effective in the methods of the present invention will depend on the specific ligand to be determined and whether the change in the transmittive properties to be measured is due to the change in the color or turbidity of the assay solution. In a colorimetric assay, that is, wherein the change in color of the assay solution is related to the change in the transmittive properties of the assay solution, a chromogenic reagent system is employed as the reagent system. In a turbidimetric or nephelometric assay wherein the turbidity, that is, the amount of light blocked or scattered by a suspension of particles, is related to the change in the transmittive properties of the assay solution, a turbidimetric reagent system or a nephelometric reagent system, respectively, is employed.

The term "chromogenic reagent system" as used herein, refers to a chemical system containing one or more reagents which will react in accordance with a specific reaction sequence with the ligand to be determined, to produce a detectable change in the transmittive properties, in particular the colorimetric properties of an assay solution within a wavelength band that overlaps the excitation and/or emission wavelength bands of the fluorescer. For the purposes of the present invention, the various reagents comprising such chromogenic reagent systems may be added individually or in any combination to the assay solution, unless the order of addition is limited by the particular reaction sequence. The chromogenic reagent systems utilized for colorimetrically determining ligands are well known in the art, for example, Henry, et al., *Clinical Chemistry, Principles and Techniques;* New York, Hoeber Medical Division, Harper & Row (1964); Tietz, *Fundamentals of Clinical Chemistry,* W. B. Saunders Company (1970). Various assay kits and reagent systems are commercially available and employ standard techniques and reagents. In general, those colorimetric procedures rely on the principle that a ligand will react with a chromogenic reagent system containing a color producing reagent, to produce a detectable color change in the assay solution. Representative chromogenic reagent systems include for example, oxidase reaction systems, including end point and kinetic determinations, and NADH/NAD reaction systems. For example, an oxidase reaction system utilized oxidative enzymes to react with the ligand to release hydrogen peroxide which subsequently reacts with a dye in the presence of peroxidase to produce a change in the colorimetric properties of the assay solution as an indication of the amount of ligand in the sample. An NADH/NAD reaction system relys upon the reduction of NAD to NADH or the oxidation to NADH to NAD and the subsequent reaction with a dye system to produce a change in the colorimetric properties of the assay solution as a measure of the concentration of ligand in the sample. The term "effective amount of reagent system" as used herein, refers to an amount of reagent system sufficient in the presence of a ligand to produce a detectable change in the colorimetric properties of the assay solution. Such effective amounts are readily ascertained by one of ordinary skill in the art.

The following serves to illustrate some of the various chromogenic reagent systems and the reaction sequences involved which may be utilized in accordance with the method of the present invention. The following abbreviations are utilized herein:

| | |
|---|---|
| DHBS | 3,5-dichloro-2-hydroxybenzene sodium sulfonate |
| AAP | 4-aminoantipyrine |
| HRPO | horseradish peroxidase |
| NAD | oxidized nicotinamide-adenine dinucleotide |
| NADH | reduced nicotinamide-adenine dinucleotide |
| LDH | lactate dehydrogenase |
| SGOT | serum glutamic oxalacetic transaminase |
| SGPT | serum glutamic pyruvic transaminase |
| CPK | creatine phosphokinase |
| INT | 2-(p-iodophenyl)-3-(p-nitrophenyl)-5-phenyltetrazolium chloride |

| ATP | adenosine triphosphate |
| ADP | adenosine diphosphate |
| EGTA | ethyleneglycol-bis(β-amino-ethylether)-N,N'-tetracetic acid |

In addition, because of the uncertainty of the specific structure of the product in some of the following reaction sequences, a product of a particular reaction sequence that produces the color of the assay solution and is measured in a spectrophotometric assay, unless specifically identified, is generally referred to herein as a "chromogen". In reaction sequence 11-16 illustrating NADH/NAD systems, the product that produces the color of the assay solution is formazine. In reaction sequence 21, illustrating an assay for blood urea nitrogen, the product that produces the color of the assay solution is indophenol. In reaction sequence 24 illustrating an assay for chloride, the product that produces the color of the assay solution is ferric thiocyanate.

1. Ligand: glucose
   Chromogenic Reagent System:
   glucose oxidase
   DHBS
   AAP
   HRPO Reaction Sequence:

D-glucose + $O_2$ + $H_2O$ $\xrightarrow{\text{glucose oxidase}}$ D-gluconic acid + $H_2O_2$ $2H_2O_2$ + DHBS + AAP $\xrightarrow{\text{HRPO}}$ chromogen 2. Ligand: Uric Acid
   Chromogenic Reagent System:
   uricase
   DHBS
   AAP
   HRPO Reaction Sequence:

Uric Acid + $O_2$ + $2H_2O$ $\xrightarrow{\text{uricase}}$ allantoin + $CO_2$ + $H_2O_2$ $2H_2O_2$ + DHBS + AAP $\xrightarrow{\text{HRPO}}$ chromogen 3. Ligand: Cholesterol (Cholesterol and Cholesterol Esters)
   Chromogenic Reagent System:
   cholesterol esterase
   cholesterol oxidase
   DHBS
   AAP
   HRPO Reaction Sequence:

Cholesterol esters $\xrightarrow{\text{Cholesterol esterase}}$ cholesterol

Cholesterol + $O_2$ $\xrightarrow{\text{Cholesterol oxidase}}$ $\Delta^4$ cholesterone + $H_2O_2$ $2H_2O_2$ + DHBS + AAP $\xrightarrow{\text{HRPO}}$ chromogen 4. Ligand: Creatinine
   Chromogenic Reagent System:
   creatininase
   creatinase
   sarcosine oxidase
   DHBS
   AAP
   HRPO Reaction Sequence:

Creatinine + $H_2O$ $\xrightarrow{\text{creatininase}}$ creatine creatine + $H_2O$ $\xrightarrow{\text{creatinase}}$ sarcosine + urea sarcosine + $H_2O$ + $O_2$ $\xrightarrow{\text{sarcosine oxidase}}$ glycine + HCHO + $H_2O_2$ $2H_2O_2$ + DHBS + AAP $\xrightarrow{\text{HRPO}}$ chromogen 5. Ligand: Lactate
   Chromogenic Reagent System:
   NAD
   LDH
   pyruvate oxidase
   DHBS
   AAP
   HRPO Reaction Sequence:

Lactate + NAD $\xrightleftharpoons{\text{LDH}}$ pyruvate + NADH pyruvate + $O_2$ $\xrightarrow{\text{pyruvate oxidase}}$ acetylphosphate + $CO_2$ + $H_2O_2$ $2H_2O_2$ + DHBS + AAP $\xrightarrow{\text{HRPO}}$ chromogen 6. Ligand: Triglycerides
   Chromogenic Reagent System:
   lipase
   glycerol kinase
   glycerol phosphate oxidase
   DHBS
   AAP
   HRPO Reaction Sequence:

Triglyceride + $3H_2O$ $\xrightarrow{\text{lipase}}$ glycerol + fatty acids glycerol + ATP $\xrightarrow{\text{glycerol kinase}}$ glycerol-3-phosphate + ADP glycerol-3-phosphate $\xrightarrow{\text{glycerol phosphate oxidase}}$ dihydroxyacetonephosphate + $H_2O_2$ $2H_2O_2$ + DHBS + AAP $\xrightarrow{\text{HRPO}}$ chromogen 7. Ligand: Cholinesterase
   Chromogenic Reagent System:
   acetylcholinesterase
   choline oxidase
   DHBS
   AAP
   HRPO Reaction Sequence:

Acetylcholine $\xrightarrow{\text{acetylcholinesterase}}$ choline + acetate choline + $O_2$ $\xrightarrow{\text{choline oxidase}}$ $2H_2O_2$ $2H_2O_2 + DHBS + AAP \xrightarrow{HRPO}$ chromogen 8. Ligand: SGOT
   Chromogenic Reagent System:
   asparate
   α-ketoglutarate
   oxalocetatedecarboxylase
   pyruvate oxidase
   DHBS
   AAP
   HRPO Reaction Sequence:

Asparate + α-ketoglutarate $\xrightarrow{SGOT}$
   glutamate + oxaloacetate oxaloacetate $\xrightarrow{\text{oxaloacetate decarboxylase}}$ pyruvate + $CO_2$ pyruvate + $O_2$ $\xrightarrow{\text{pyruvate oxidase}}$ $H_2O_2$ + acetylphosphate + $CO_2$ $2H_2O_2 + DHBS + AAP \xrightarrow{HRPO}$ chromogen 9. Ligand: SGPT
   Chromogenic System:
   L-alanine
   α-ketoglutarate
   pyruvate oxidase
   DHBS
   AAP
   HRPO Reaction Sequence:

Alanine + α-ketoglutarate $\xrightarrow{SGPT}$ glutamate + pyruvate pyruvate + $O_2$ $\xrightarrow{\text{pyruvate oxidase}}$ acetylphosphate + $H_2O_2$ + $CO_2$ $2H_2O_2 + DHBS + AAP \xrightarrow{HRPO}$ chromogen 10. Ligand: CPK
    Chromogenic System:
    Creatine phosphate
    creatinase
    sarcosine oxidase
    DHBS
    AAP
    HRPO Reaction Sequence:

Creatine phosphate + ADP $\xrightarrow{CPK}$ creatine + ATP creatine + $H_2O$ $\xrightarrow{\text{creatinase}}$ sarcosine + urea sarcosine + $H_2O$ + $O_2$ $\xrightarrow{\text{sarcosine oxidase}}$ glycine + $H\overset{O}{\overset{\|}{C}}H$ + $H_2O_2$ $2H_2O_2 + DHBS + AAP \xrightarrow{HRPO}$ chromogen 11. Ligand: Ethanol
    Chromogenic Reagent System:
    NAD
    alcohol dehydrogenase
    INT
    diaphorase Reaction Sequence:

Ethanol + NAD $\xrightarrow{\text{alcohol dehydrogenase}}$ NADH + acetaldehyde

NADH + INT $\xrightarrow{\text{diaphorase}}$ NAD + formazine

12. Ligand: SGOT
    Chromogenic Reagent System:
    asparatate
    α-ketoglutarate
    NAD
    glutamate dehydrogenase
    diaphorase
    INT Reaction Sequence:

Asparate + α-ketoglutarate $\xrightarrow{SGOT}$
    glutamate + oxaloacetate

NAD + glutamate + $H_2O$ $\xrightarrow{\text{glutamate dehydrogenase}}$
    NADH + 2-oxoglutarate + $NH_3$ NADH + INT $\xrightarrow{\text{diaphorase}}$ NAD + formazine 13. Ligand: SGPT
    Chromogenic Reagent System:
    L-alanine
    α-ketoglutarate
    NAD
    glutarate dehydrogenase
    diaphorase
    INT Reaction Sequence:

Alanine + α-ketoglutarate $\xrightarrow{SGPT}$ glutamate + pyruvate glutamate + NAD + $H_2O$ $\xrightarrow{\text{glutamate dehydrogenase}}$
    NADH + 2-oxoglutarate + $NH_3$ NADH + INT $\xrightarrow{\text{diaphorase}}$ NAD + formazine 14. Ligand: Glucose
    Chromogenic Reagent System:
    ATP
    hexokinase
    NAD
    glucose-6-phosphate dehydrogenase
    INT
    diaphorase Reaction Sequence:

Glucose + ATP $\xrightarrow{\text{hexokinase}}$ glucose-6-phosphate + ADP glucose-6-phosphate + NAD $\xrightarrow{\text{glucose-6-phosphate dehydrogenase}}$
    NADH + gluconate-6-phosphate NADH + INT $\xrightarrow{\text{diapharose}}$ NAD + formazine 15. Ligand: CPK
    Chromogenic Regent System:
    Creatine phosphate
    ADP
    glucose
    hexokinase
    NAD
    glucose-6-phosphate dehydrogenase
    INT -continued diaphorase Reaction Sequence:

Creatine phoxphate + ADP $\xrightarrow{CPK}$ creatine + ATP glucose + ATP $\xrightarrow{hexokinase}$ glucose-6-phosphate + ADP glucose-6-phosphate + NAD $\xrightarrow{\text{glucose-6-phosphate dehydrogenase}}$ NADH + gluconate-6-phosphate NADH + INT $\xrightarrow{diaphorase}$ NAD + formazine 16.               Ligand: LDH
Chromogenic Reagent System:
L-lactate
NAD
INT
diaphorase Reaction Sequence:

L-lactate + NAD $\xrightleftharpoons{LDH}$ NADH + pyruvate

NADH + INT $\xrightarrow{diaphorase}$ NAD + formazine

17.              Ligand: Total Protein
Chromogenic Reagent System:
copper tartrate
sodium tartrate
lithium acetate Reaction Sequence:
Protein + copper tartrate + sodium tartrate + lithium hydroxide $\longrightarrow$ chromogen 18. Ligand: Albumin
Chromogenic Reagent System:
Bromcresol green Reaction Sequence:

Albumin + bromcreosol green $\longrightarrow$ chromogen

19. Ligand: Calcium
Chromogenic Reagent System:
o-cresolphthalein complexon
8-quinolino sulfate Reaction Sequence:

Calcium + o-cresolphthalein + 8-quinolinol sulfate $\longrightarrow$ chromogen

20. Ligand: Bilirubin
Chromogenic Reagent System:
diazonium salt of 2,4-di-chloroaniline
methanol
sulfamic acid Reaction Sequence:
Bilirubin + diazonium salt of 2,4-dichloroaniline $\xrightarrow[\text{sulfamic acid}]{\text{methanol}}$ chromogen 21. Ligand: Blood Urea Nitrogen (Urea)
Chromogenic Reagent System:
urease
sodium hypochlorite
phenol
sodium hydroxide
sodium nitroprusside Reaction Sequence:

Urea $\xrightarrow{urease}$ 2HN$_3$ + CO$_2$

2NH$_3$ + 2NaClO $\longrightarrow$ 2NH$_2$Cl + 2NaOH

2NH$_2$Cl + 2 phenol + 2NaOH $\longrightarrow$ 2p-aminophenol + 2NaCl + 2H$_2$O 2p-aminophenol + 2 phenol + O$_2$ $\longrightarrow$ 2 indophenol + 2H$_2$O 22. Ligand: Magnesium
Chromogenic Reagent System:
potassium chloride
calmagite
potassium cyanide
potassium hydroxide
EGTA Reaction Sequence:

Magnesium + KCl + calmagite + KCN $\xrightarrow[EGTA]{KOH}$ chromogen

23. Ligand: Phosphorous
Chromogenic Reagent System:
molybdic acid
sulfuric acid
catalyst Reaction Sequence:

Phosphate + molybdic acid + sulfuric acid $\xrightarrow{catalyst}$ chromogen

24. Ligand: Chloride
Chromogenic Reagent System:
urea
potassium thiocyanate
mecuric chloride
perchloric acid
mercuric perchlorate
ferric perchlorate Reaction Sequence:

2 Cl$^-$ + Hg(SCN)$_2$ $\longrightarrow$ HgCl$_2$ + 2 SCN$^-$

3 SCN$^-$ + Fe$^{++}$ $\longrightarrow$ Fe(SCN)$_3$

The term "turbidimetric reagent system" as used herein refers to a chemical system containing one or more reagents that will interact in accordance with a specific procedure with the ligand to be determined to produce a detectable change in the transmittive properties, in particular the turbidity, of an assay solution within a wavelength band that overlaps the excitation and/or emission wavelength band of a fluorescer. For the purpose of the present invention, the various reagents comprising turbidimetric reagent systems may be added individually or in any combination to the assay solution, unless the order of addition is limited by the particular reaction sequence. Various turbidimetric reagent systems are well known in the art. One important class of assays utilizing a turbidimetric reagent system includes assays to turbidimetrically measure human immunoglobulins. The principle upon which such assays rely is based upon the formation of a specific complex consisting of a suspension of particles, due to the reaction of a turbidimetric reagent system consisting of antiserum specific to the immunoglobulin to be determined, and the immunoglobulin of interest. The suspension of particles due to the formation of an antiserum-immunoglobulin complex produces in a change in the turbidity of the assay solution. Therefore, if an excess of antiserum over human immunoglobulin is employed in the assay solution, the light transmitted through the suspension decreased as the concentration of immunoglobulin in the sample increases. The term "nephelometric reagent system" as used herein refers to a chemical system containing one or more reagents that will interact in accordance with a specific procedure with the ligand to be determined to produce a detectable change in the transmittive properties, in particular the turbidity, of the assay solution, within a wavelength band that overlaps the excitation and/or emission bands of a fluorescer. Nephelometric assays rely upon the same principles as terbidimetric assays except that nephelometric measurements of an assay solution unlike turbidimetric measurements, measure the scattered light at an angle to the incident light. Numerous turbidimetric and nephelometric assays are known in the art and the reagent systems employed in such assays are readily ascertained by one of ordinary skill in the art.

In carrying out the method of the present invention the assay solution is introduced into a fluorometer cell. The choice of excitation wavelength will depend on the fluorescer, ligand and reagent system utilized. The particular wavelength or band wavelength which is measured for the emission spectrum will generally depend upon the emission maximum. By determining the emission spectrum employing a light source of constant intensity, and observing the emission intensity at a particular wavelength or particular band of wavelength, one can relate this result to known standards. By carrying out the assay procedure of the present invention with an unknown in substantially the same manner as with standards containing known amounts of the ligand to be determined, a qualitative or quantitative determination of the amount of ligand present in the unknown sample may be achieved.

Although the concentration of ligand which may be determined in acccordance with the methods of the present invention depends in a large part upon the specific fluorometer employed and the specific reagent system utilized, samples containing ligands in a concentration range as low as 0.01–0.1 mM have been determined.

The pH of the assay solution is generally dependent upon the specific reagent system employed. The pH of the reagent system will be a factor in the choice of a fluorescer in that it is necessary that the fluorescer emit fluorescence within the pH range of the reagent system.

With certain ligands and fluorescers, there may be small but insignificant amounts of nonspecific binding of the ligands and fluorescer to proteins. If protein interference is a factor, it is preferred that the protein concentration of the assay solution be minimized by prior treatment of the sample by ultrafiltration, gel filtration, precipitation, dialysis, and the like. In addition, nonspecific binding of the ligands or fluorescers to proteins may be minimized upon the addition of a surfactant such as Triton X-100 or the like, to the assay solution.

The method of the present invention is generally conducted within a temperature range from about 15°–40° C., and preferably, from about 25°–40° C. It is also preferred that the assay be conducted at a constant temperature.

The following examples serve to illustrate the method of the present invention. The concentration of reagents and other variable parameters are only shown to exemplify the method of the present invention and are not to be considered as limitations thereof. Assays employing commercial kits, i.e., Abbott A-Gent TM clinical chemistry reagents, are generally utilized as the reagent system in accordance with the package inserts provided with the kit. The only additional reagent added is the particular fluorescer employed. Also, in the following examples, the fluorescence intensity $(F_i)$ of each assay solution is measured utilizing an Abbott $Td_x$ ® analyzer at a wavelength of 485 nm for excitation and 525 nm for emission. In the following examples, a standard curve may be prepared by plotting the fluorescence intensity measured for each standard solution versus the concentration of the standard solution. In addition, if a straight line standard curve is desired, one plots the negative of the logrithm of the fluorescence intensity measured for each standard solution versus the concentration of the standard solution.

EXAMPLE 1

Glucose Assay

To 5 μl of a sample containing an unknown or glucose standard was added 2.05 ml of a phosphate buffer with bovine gammaglobulin (pH 7.5) containing 25 μl of a solution containing 2200 units/ml of glucose oxidase; 25 μl of a solution containing 0.2M DHBS and $10^{-5}$M fluorescein; and 25 μl of a solution containing 0.1% 4-aminoantipyrene and 400 units/ml of horseradish peroxidase. The resulting assay solution was allowed to proceed at 35° C., until color production was maximized. The absorbance and fluorometric intensity were measured and the results obtained for standards containing from 0–500 mg/dl glucose are represented in the following table:

| Glucose Concentration (mg/dl) | Absorbance (1 cm path length) Wavelength | | | Fluorescent Intensity $(F_i)$ |
|---|---|---|---|---|
| | 485 nm | 500 nm | 525 nm | 525 nm |
| 0 | 0.026 | 0.016 | 0.003 | 55,129 |
| 50 | 0.117 | 0.129 | 0.119 | 43,035 |
| 100 | 0.205 | 0.236 | 0.227 | 34,141 |
| 200 | 0.392 | 0.469 | 0.465 | 21,010 |
| 300 | 0.577 | 0.697 | 0.695 | 13,106 |
| 500 | 0.836 | 1.016 | 1.019 | 5,960 |

From these results a standard curve may be prepared from which glucose concentration in unknown samples may be determined.

EXAMPLE 2

Uric Acid Assay

To 20 μl of a sample containing an unknown or uric acid standard was added 2.05 ml of a phosphate buffer with bovine gammaglobulin (pH 7.5) containing 25 μl of a solution containing 10 units/ml of uricase; 25 μl of a solution containing 0.2M DHBS and $10^{-5}$M fluorescein; and 25 μl of a solution containing 0.1% 4-aminoantipyrene and 400 units/ml of horseradish peroxidase.

The resulting assay solution was allowed to incubate at 35° C. for five minutes and the fluorescence intensity of the assay solution was measured. The results obtained from samples containing from 0–9 mg/dl uric acid are represented in the following table:

| Uric Acid Concentration (mg/dl) | $F_I$ |
|---|---|
| 0 | 57,588 |
| 2 | 54,440 |
| 4 | 52,431 |
| 5 | 51,426 |
| 6 | 50,774 |
| 9 | 47,767 |

From these results, a standard curve may be prepared from which uric acid concentration in unknown samples may be determined.

The following table represents the concentration of uric acid determined for Dade Moni-Trol I and II chemistry control samples using a standard curve prepared from the results in the above table.

| Sample No. | Reported Control Value (mg/dl) | Concentration of Uric Acid Determined (mg/dl) |
|---|---|---|
| Moni-Trol I | 4.1 | 4.0 |
| Moni-Trol II | 9.5 | 8.4 |

EXAMPLE 3

Cholesterol Assay

To 10 μl of a sample containing an unknown or cholesterol standard was added 2.05 ml of a solution containing phosphate buffer with bovine gammaglobulin pH 7.5, also containing 25 μl of a solution containing 1100 units/ml of cholesterol esterase, 100 units/ml of cholesterol oxidase, 20% Triton X-100, and 0.2M cholate; 25 μl of a solution containing approximately $1 \times 10^{-5}$M fluorescein and 0.2M DHBS; 25 μl of a solution containing 0.1% 4-aminoantipyrene and 400 μ/ml horseradish peroxidase.

The resulting assay solution was allowed to incubate at 35° C. for five minutes. The results obtained from standards containing from 400 mg/dl cholesterol are represented in the following table:

| Cholesterol Concentration (mg/dl) | $F_I$ |
|---|---|
| 0 | 65,175 |
| 50 | 56,909 |
| 100 | 49,998 |
| 200 | 38,404 |
| 300 | 29,149 |
| 400 | 22,273 |

From these results a standard curve may be prepared from which cholesterol concentration in unknown samples may be determined.

The following table represents the concentration of cholesterol determined for the Dade Moni-Trol I and II chemistry control samples using a standard curve prepared from the results in the above table.

| Sample No. | Reported Control Value (mg/dl) | Concentration Of Cholesterol Determined (mg/dl) |
|---|---|---|
| Moni-Trol I | 116 | 110 |
| Moni-Trol II | 220 | 212 |

EXAMPLE 4

Total Protein Assay

To 3 ml of reconstituted Abbott A-Gent ™ total protein reagent which was adjusted to contain $1.5 \times 10^{-7}$M fluorescein was added 50 μl of a sample containing an unknown or standard. The reagent and sample was mixed and allowed to incubate at 20° C. for at least 10 minutes. The fluorescent intensity of the assay solution was measured and the results obtained for standards containing from 0–8 g/dl of protein are represented in the following table:

| Protein Concentration (g/dl) | $F_I$ |
|---|---|
| 0 | 54,068 |
| 4 | 37,383 |
| 6 | 32,760 |
| 8 | 27,792 |

From these results a standard curve may be prepared from which total protein concentration in unknown samples may be determined.

EXAMPLE 5

LDH Assay

To 20 μl of a sample containing an unknown or standard was added $2.0 \times 5$ ml of a phosphate buffer with bovine gammaglobulin (pH 7.5) containing 25 μl of a solution containing 250 mg/ml lithium-L-lactate and 125 mg/ml NAD; 25 μl of a solution containing 25 mg/ml INT and $1 \times 10^{-5}$M fluorescein in 50% ethanol and 25 μl of 100 units/ml Diaphorase in 50% glycerol. The sample and reagent solution were mixed and the resulting assay solution was allowed to incubate for fourteen minutes at 35° C. The fluorescence intensity of the assay solution was measured. The results obtained for standards containing from 0–500 units/l of LDH were represented in the following table:

| LDH Activity (units/ml approximately) | $F_I$ |
|---|---|
| 0 | 45,797 |
| 50 | 43,170 |
| 100 | 41,470 |
| 200 | 38,484 |
| 300 | 35,909 |
| 500 | 28,021 |

From these results a standard curve may be prepared from which LDH concentration in unknown samples may be determined.

EXAMPLE 6

Creatinine Assay

To 20 ml of an aqueous solution containing 5.5 ml of picric acid and 1.1 ml of 2.5N sodium hydroxide was added 200 μl of $10^{-5}$M fluorescein to yield a reagent solution containing $10^{-7}$M fluorescein. To 2 ml of the above prepared reagent solution was added 100 μl of a sample containing an unknown or standard. The resulting assay solution was incubated at 35° C. for approximately 15 minutes and the fluorescent intensity of the assay solution was measured. The results obtained for standards containing from 0–10 mg/dl creatinine are represented in the following table:

| Creatinine Concentration (mg/dl) | $F_I$ |
| --- | --- |
| 0 | 8282 |
| 2 | 7665 |
| 6 | 6159 |
| 10 | 4972 |

From these results a standard curve may be prepared from which creatinine concentration in unknown samples may be determined.

EXAMPLE 7

BUN Assay

To 20 μl of a sample containing an unknown or standard was added 2.050 ml of a reagent solution comprising 0.1M potassium phosphate (pH 7.5) buffer; bovine gamma globulin; 0.1% sodium azide; 25 μl of a 5% glycerol solution containing 130 units/ml urease; 25 μl of a $10^{-5}$M fluorescein solution prepared by adding 300 mg of sodium nitroprusside in 1 ml of water to 5 ml of phenol, 1 ml of glycerol and 1 ml of ethanol and sufficient fluorescein to yield a final concentration of $10^{-5}$M fluorescein; and 25 μl of a solution prepared by adding 25 g of sodium hydroxide to 50 ml of a solution containing 5.7% sodium hydrochlorite. The sample and reagent solution were mixed and the resulting assay solution was allowed to incubate for approximately 5 minutes at 35° C. The fluorescence intensity of the assay solution was measured. The results obtained for standards containing from 0–100 mg/dl of urea are represented in the following table:

| Urea Concentration (mg/dl) | $F_I$ |
| --- | --- |
| 0 | 31847 |
| 6.25 | 28713 |
| 12.5 | 25745 |
| 25 | 20962 |
| 50 | 15538 |
| 100 | 8798 |

From these results a standard cruve may be prepared from which urea concentration in unknown samples may be determined.

EXAMPLE 8

Bilirubin Assay

To 2 ml of reconstituted Abbott A-Gent TM bilirubin reagent which was adjusted to contain $10^{-7}$M fluorescein was added 50 μl of a sample containing an unknown or standard. The reagent and sample were mixed and allowed to incubate at 37° C. for approximately ten minutes. The fluorescent intensity of the resulting assay solution was measured and the results obtained for standards containing from 0–20.2 mg/dl of bilirubin are represented in the following table:

| Bilirubin Concentration (mg/dl) | $F_I$ |
| --- | --- |
| 0 | 65,256 |
| 4 | 59,371 |
| 10.1 | 50,353 |
| 20.2 | 32,740 |

From these results a standard curve may be prepared from which bilirubin concentration in unknown samples may be determined.

The following table represents the concentration of bilirubin determined for Dade Moni-Trol I and II chemistry control samples using a standard curve prepared from the results in the above table:

| Sample No. | Reported Control Value (mg/ml) | Concentration Of Bilirubin Determined (mg/ml) |
| --- | --- | --- |
| Moni-Trol I | 1.2 | 1.1 |
| Moni-Trol II | 4.0 | 4.5 |

EXAMPLE 9

Calcium Assay

To 3 ml of reconstituted Abbott A-Gent TM calcium reagent which was adjusted to contain $1.5\times10^{-7}$M fluorescein was added 100 μl of a sample containing an unknown or calcium standard. The reagent and sample were mixed and allowed to incubate at 20° C. for approximately 10 minutes. The fluorescent intensity of the assay solution was measured and the results obtained for standards containing from 0–12 mg/dl of calcium are represented in the following table:

| Calcium Concentration (mg/dl) | $F_I$ |
| --- | --- |
| 0 | 41,881 |
| 8 | 30,762 |
| 10 | 29,029 |
| 12 | 26,416 |

From these results a standard curve may be prepared from which calcium concentration in unknown samples may be determined.

EXAMPLE 10

Albumin Assay

To 2 ml of reconstituted Abbott A-Gent TM albumin reagent which was adjusted to contain $5\times10^{-5}$M brilliant sulfaflavin was added 10 μl of a sample containing an unknown or standard. The reagent and sample were mixed and allowed to incubate for five minutes at 20° C. The fluorescent intensity of the resulting assay solution was measured and the results obtained for standards containing from 0–8 g/dl of albumin are represented in the following table:

| Albumin Concentration (g/dl) | $F_I$ |
| --- | --- |
| 0 | 2,888 |
| 3 | 2,430 |

| Albumin Concentration (g/dl) | $F_I$ |
|---|---|
| 8 | 2,056 |

From these results a standard curve may be prepared from which albumin concentration in unknown samples may be determined.

EXAMPLE 11

Chloride Assay

To 2 ml of Harleco ® Chloride Developing Reagent which was adjusted to contain $5\times10^{-5}$M brilliant sulfaflavin was added 20 μl of a sample containing an unknown or standard. To the resulting mixture was added one drop of a 0.2M mercuric perchlorate solution and the fluorescent intensity of the resulting assay solution was measured. The results obtained for standards containing from 0-200 meq/l of chloride are represented in the following table:

| Chloride Concentration (meq/l) | $F_I$ |
|---|---|
| 0 | 54,047 |
| 50 | 48,959 |
| 100 | 23,900 |
| 200 | 10,368 |

From these results a standard curve may be prepared from which chloride concentration in unknown samples may be determined.

The following table represents the chloride concentration obtained for Dade Moni-Trol I and II chemistry control samples using a standard curve prepared from the results in the above table.

| Sample No. | Reported Control Value (meq/l) | Chloride Concentration (meq/l) |
|---|---|---|
| Moni-Trol I | 112 | 110 |
| Moni-Trol II | 96 | 85 |

EXAMPLE 12

Magnesium Assay

To 1.0 ml of a magnesium dye reagent (P.L. Biochemicals, Inc.) which was adjusted to contain $5\times10^{-7}$M fluorescein was adding 1.0 ml of magnesium base reagent (P.L. Biochemical, Inc.) and 20 μl of a sample containing an unknown or standard. The resulting assay solution was allowed to stand for at least one minute at 20° C. and the fluorescent intensity of the assay solution was measured. The results obtained for standards containing from 0-6.0 meq/l magnesium are represented in the following table:

| Magnesium Concentration (meq/l) | $F_I$ |
|---|---|
| 0 | 31,612 |
| 2.0 | 22,510 |
| 4.0 | 17,330 |
| 6.0 | 12,802 |

From these results a standard curve may be prepared from which magnesium concentration in unknown samples may be determined.

The following table represents the concentration of magnesium determined for a Dade Moni-Trol I chemistry control sample using a standard curve prepared from the results in the above table:

| Sample No. | Reported Control Value (meq/l) | Magnesium Concentration (meq/l) |
|---|---|---|
| Moni-Trol I | 2.1 | 2.2 |

EXAMPLE 13

Glucose Assay

To 5 μl of a sample containing an unknown or glucose standard was added 2.05 ml of a phosphate buffer with bovine gammaglobulin (pH 7.0) containing 25 μl of a solution containing 2200 units/ml of glucose oxidase 0.025 mg/ml thimersol and 1.5M ammonium sulfate, 25 μl of a solution containing 0.2M DHBS, 0.1% potassium ferricyanide, 0.1% 4-aminoantipyrene, 0.1% triton X-100, 0.025 mg/ml thimersol and $5.633\times10^{-4}$ mol/l riboflavin in 0.1M phosphate buffer; and 25 μl of a solution containing 400 units/ml of horseradish peroxidase 10% calf serum, 0.6 mM EDTA, 0.1% ANS, 1% triton X-100, 2000 units/ml lipase, 0.025 g/ml thimersol in 0.1M phosphate buffer. The resulting assay solution was allowed to proceed at 35° C., until color production was maximized. The absorbance and fluorometric intensity was measured and the results obtained for standards containing from 0-500 mg/dl glucose are represented in the following table:

| Glucose Concentration (mg/dl) | $F_I$ |
|---|---|
| 0 | 37,432 |
| 50 | 28,731 |
| 100 | 22,019 |
| 200 | 12,547 |
| 300 | 7,291 |
| 500 | 2,269 |

EXAMPLE 14

Immunoglobulin G (IgG) Assay

To 2.5 ml of a working antiserum reagent prepared by mixing 400 μl of goat anti-human IgG antiserum with 11.6 ml of a phosphate buffered saline solution containing 4% polyethyleneglycol using the reagents supplied in the Abbott A-Gent ™ Immunoglobulin G clinical chemistry diagonstic kit, was added 100 μl of standard solutions prepared in accordance with the instructions in the Abbott A-Gent ™ Immunoglobulin G clinical chemistry diagnostic kit using the standard supplies with the kit. To the mixture was added 25 μl of a $10^{-5}$M fluorescein solution and the fluorescent intensity of the assay solution was measured and the results obtained from the standards containing from 382–6093 ng/dl of immunoglobulin G are represented in the following table:

| IgG Concentration (ng/dl) | $F_I$ |
|---|---|
| 382 | 10,556 |
| 761 | 10,262 |
| 1526 | 10,132 |
| 3046 | 9,397 |
| 6093 | 8,849 |

As evidenced in the preceeding examples, the method of the present invention is adaptable to a wide variety of assay systems. In addition to providing the capability of fluorometrically determining an unknown ligand utilizing known chromogenic reagent systems, the method of the present invention increases the linearity of an assay employing chromogenic reagent systems. In particular, the method of the present invention increases the linearity ranges of assays at high absorbance values. It is well known that due to instrumentation limitations, the linearity of colorimetric assays decreases substantially at chromogen concentrations having absorbance values greater than 2.0. Using the methods of the present invention, it is possible to extend linearity of an assay using concentrations of reagent system and ligand that result in a chromogen concentration having an absorbance value greater than 2.0.

As previously mentioned, the present invention relates to novel reaent compositions which may be utilized to either spectrophotometrically or fluorometrically measure the concentration of a ligand in an assay solution. Such reagent compositions comprise an effective amount of a reagent system specific for the ligand, that is, a reagent system capable of providing a change in the transmittive properties of a solution containing the ligand to be determined, and an effective amount of a fluorescer having an excitation and/or emission wavelength band that overlaps the wavelength band associated with the change in the transmittive properties of a solution containing the reagent system and the ligand to be determined. It has been found that the effective amount of fluorescer required to produce a reagent composition useful to determine a ligand fluorometrically in accordance with the method of the present invention, does not interfere with the measurement of the transmittive properties of the assay solution. Therefore, an assay solution containing the ligand to be determined and reagent composition of the present invention specific for the ligand, may be spectrophotometrically or fluorometrically measured to determine the concentration of the ligand in the assay solution.

Although this invention has been described with respect to specific embodiments, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for determining a ligand in a sample suspected of containing the ligand, said method comprising:
   (a) combining to form an assay solution
      (i) said sample;
      (ii) an effective amount of a fluorescer which does not react chemically or immunologically with the ligand;
      (iii) an effective amount of a reagent system which does not react either chemically or immunogically with the fluorescer and which in the presence of the ligand to be determined is capable of providing a change in the transmittive properties of the assay solution within a wavelength band that overlaps the excitation and/or emission wavelength band of the fluorescer and
   (b) irradiating the assay solution with light having a wavelength within the excitation wavelength band of the fluorescer; and then
   (c) measuring the intensity of the fluorescence emitted by the assay solution as a measure of the concentration of the ligand in the sample.

2. A method according to claim 1 wherein the reagent system is a chromogenic reagent system or a turbidimetric reagent system.

3. A method according to claim 2 wherein the reagent system is a chromogenic reagent system.

4. A method according to claim 3 wherein the absorption wavelength band associated with the change in the transmittive properties of the assay solution overlaps the excitation wavelength band of the fluorescer.

5. A method according to claim 3 wherein the absorption wavelength band associated with the change in the transmittive properties of the assay solution overlaps the emission wavelength band of the fluorescer.

6. A method according to claim 3 wherein the absorption wavelength band associated with the change in the transmittive properties of the assay solution overlaps the excitation and emission wavelength bands of the fluorescer.

7. An improved fluorimetric assay method for determining a ligand in an assay solution containing a sample suspected of containing the ligand, and an effective amount of a reagent system which in the presence of the ligand is capable of providing a change in the transmittive properties of the assay solution within a wavelength band, said improvement comprising adding to the assay solution an effective amount of a fluorescer wherein the fluorescer does not react either chemically or immunologically with the ligand or the reagent system, and wherein the excitation and/or emission wavelength band of the fluorescer overlaps the wavelength band associated with the change in the transmittive properties of the assay solution; irradiating the assay solution with light having a wavelength within the excitation wavelength band of the fluorescer; and then measuring the intensity of the fluorescer emitted by the assay solution as a measure of the concentration of the ligand in the sample.

8. A method according to claim 7 wherein the reagent system is a chromogenic reagent system or a turbidimetric reagent system.

9. A method according to claim 8 wherein the reagent system is a chromogenic reagent system.

10. A method according to claim 9 wherein the fluorescer has an excitation wavelength band that overlaps the absorption wavelength band associated with the change in the transmittive properties of the assay solution.

11. A method according to claim 9 wherein the fluorescer has an emission wavelength band that overlaps the absorption wavelength band associated with the change in the transmittive properties of the assay solution.

12. A method according to claim 9 wherein the fluorescer has an excitation wavelength band and emission wavelength band that overlap the absorption wavelength band associated with the change in the transmittive properties of the assay solution.

* * * * *

REEXAMINATION CERTIFICATE (1335th)

United States Patent [19]

Shaffar

[11] B1 4,495,293

[45] Certificate Issued Jul. 31, 1990

[54] FLUOROMETRIC ASSAY

[75] Inventor: Mark R. Shaffar, Vernon Hills, Ill.

[73] Assignee: Abbott Laboratories, Chicago, Ill.

Reexamination Request:
No. 90/001,697, Jan. 23, 1989

Reexamination Certificate for:
Patent No.: 4,495,293
Issued: Jan. 22, 1985
Appl. No.: 469,323
Filed: Feb. 24, 1983

[51] Int. Cl.$^5$ .................. G01N 21/17; G01N 21/25
[52] U.S. Cl. ......................... 436/172; 250/461.1; 436/501; 436/537; 436/800
[58] Field of Search ............... 436/172, 537, 546, 800

[56] References Cited

U.S. PATENT DOCUMENTS

| | | | |
|---|---|---|---|
| 3,874,853 | 4/1975 | Byrnes | 23/230 |
| 4,095,948 | 6/1978 | Hunziker | 23/230 |
| 4,273,556 | 6/1981 | Gindler | 23/230 |

OTHER PUBLICATIONS

Tietz, *Fundamentals of Clinical Chemistry*, Published by W. B. Sanders Co., (1970), pp. 87–88, 107–108, 139–142.

Henry et al, *Clinical Chemistry Principles and Technics*, Second Edition, Published by Harper & Row, (1974), pp. 1125–1127.

Blumberg, W. E., Doleiden, F. H. and Lamola, A. A., "Hemoglobin Determined in 15 uL of Whole Blood by Front–Face Fluorometry." Clin. Chem. 26/3:409–413 (1980).

Toro, G. and Ackerman, P. G., "Practical Chemistry." Little, Brown and Company, Boston, Mass., pp. 8, 9 and 25 (1975).

*Primary Examiner*—Robert J. Hill, Jr.

[57] ABSTRACT

A method is provided to fluorometrically determine a ligand in an assay solution containing the ligand, reagent system and a fluorescer wherein the intensity of the fluorescer emitted by the assay solution is related to the change in the transmittive properties of the assay solution produced by the interaction of the ligand to be determined and a reagent system capable of producing a change in the transmittive properties of the assay solution in the presence of the ligand. In addition, novel reagent compositions are provided which may be utilized to either spectrophotometrically or fluorometrically determine the concentration of a ligand in an assay solution.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

* * * * *